(12) United States Patent
Xie et al.

(10) Patent No.: US 8,534,136 B2
(45) Date of Patent: Sep. 17, 2013

(54) PIN SOLDERING FOR PRINTED CIRCUIT BOARD FAILURE TESTING

(75) Inventors: Dongji Xie, San Jose, CA (US); Miao Cai, Yulin (CN); Boyi Wu, Wuhai (CN)

(73) Assignee: Flextronics AP, LLC., Broomfield, CO (US)

( * ) Notice: Subject to any disclaimer, the term of this patent is extended or adjusted under 35 U.S.C. 154(b) by 501 days.

(21) Appl. No.: 12/751,061

(22) Filed: Mar. 31, 2010

(65) Prior Publication Data

US 2011/0239775 A1   Oct. 6, 2011

(51) Int. Cl.
*G01N 3/08* (2006.01)

(52) U.S. Cl.
USPC .......................................................... 73/834

(58) Field of Classification Search
USPC .......................................................... 73/834
See application file for complete search history.

(56) References Cited

U.S. PATENT DOCUMENTS

| | | | | |
|---|---|---|---|---|
| 5,153,385 | A | * | 10/1992 | Juskey et al. ................ 174/260 |
| 5,969,262 | A | * | 10/1999 | Ino et al. ......................... 73/827 |
| 6,078,387 | A | | 6/2000 | Sykes |
| 6,178,823 | B1 | | 1/2001 | Sykes |
| 6,237,422 | B1 | | 5/2001 | Sykes |
| 6,301,971 | B1 | | 10/2001 | Sykes |
| 6,341,530 | B1 | | 1/2002 | Sykes |
| 6,395,568 | B1 | | 5/2002 | Blish et al. |
| 6,548,881 | B1 | | 4/2003 | Blish et al. |
| 6,681,640 | B2 | | 1/2004 | Canumalla |
| 6,812,578 | B2 | | 11/2004 | Kim et al. |
| 7,013,564 | B2 | | 3/2006 | Shimokawa et al. |
| 7,319,043 | B2 | | 1/2008 | Yang et al. |
| 7,444,012 | B2 | | 10/2008 | White et al. |

(Continued)

FOREIGN PATENT DOCUMENTS

| | | |
|---|---|---|
| JP | 07218405 | 8/1995 |
| JP | 10150078 | 6/1998 |
| JP | 2003188201 | 7/2003 |
| JP | 2007163147 | 6/2007 |

OTHER PUBLICATIONS

PCT/US2011/030331 Search Report and Written Opinion from the International Searching Authority, Dec. 7, 2011, 10 pages.

(Continued)

*Primary Examiner* — Lisa Caputo
*Assistant Examiner* — Octavia D. Hollington
(74) *Attorney, Agent, or Firm* — Haverstock & Owens LLP

(57) ABSTRACT

Systems and methods for performing pin-pull testing of a printed circuit board (PCB) are presented. The pin-pull testing generally involves the use of a standard tensile tester that is useful for performing other tests aside from pin-pull testing. In this regard, a non-specific pin may be used in conjunction with the tensile tester without the need to purchase or manufacture pins specially adapted for use with a specially designed tensile tester. Additionally, the pin-pull testing may include application of heat to the pin by way of an external heat supply such that the need of a heater integrated into the testing device to heat a pin during the testing may be eliminated. As such, a common heating element (e.g., a standard soldering iron) may be employed by applying heat to a pin directly with the external heat supply. Additionally, a dying process is presented that may be performed on a PCB prior to the pin-pull test that allows for evaluation of the presence of cracks in the PCB adjacent to a contact pad prior to the execution of the pin-pull test.

22 Claims, 8 Drawing Sheets

(56) References Cited

U.S. PATENT DOCUMENTS

| | | |
|---|---|---|
| 7,446,546 B2 | 11/2008 | Yang et al. |
| 7,543,507 B2 * | 6/2009 | Li et al. .......................... 73/851 |
| 8,096,837 B2 * | 1/2012 | Kan et al. ...................... 439/638 |
| 8,100,021 B2 * | 1/2012 | Sykes ............................ 73/827 |
| 2005/0018898 A1 | 1/2005 | White et al. |
| 2007/0152693 A1 | 7/2007 | Yang et al. |
| 2008/0190212 A1 | 8/2008 | Sykes |
| 2009/0151989 A1 | 6/2009 | Hunrath |

OTHER PUBLICATIONS

Mudasir Ahmad, Jennifer Burlingame, and Cherif Guirguis, Comprehensive Methodology to Characterize and Mitigate BGA Pad Catering in Printed Circuit Boards, SMTA Journal, 2009, pp. 21-28, vol. 22, Issue 1.

Robert Sykes, Pull Testing of Solder Balls on BGA and CSP Packages Without Reflow, Dage Precision Industries Ltd.

Die Alternative zum Drop Test High Speed Bondtester, www.dage.de/de/bondtest/4000hs.htm.

Pull Testing-Cold Bump Bull, www.dage-group.com/pull-testing-cold-bump-pull.

4000HS High Speed Bondtesting, www.dage-group.com.

Wire Bonding Assembly, Florida MicroElectronics, www.flmicroelec.com.

Brian Roggeman, Peter Borgesen, Jing Li, Guarave Godbole, Pushkraj Tumne, K. Srihari, Tim Levo, James Pitarresi, Assessment of PCB Pad Cratering Resistance by Joint Level Testing, Section 3.2 Cyclic Load Lifetime, 2008 Electronic Components and Technology Conference.

* cited by examiner

PIN SOLDERING FOR PRINTED CIRCUIT BOARD FAILURE TESTING

BACKGROUND

As integrated circuit (IC) device technology has become more advanced, the size of IC devices has progressively gotten smaller. Because IC devices are commonly incorporated into electronic devices by way of attachment to a printed circuit board (PCB), as IC devices have become smaller, the technology for attachment of IC devices to PCBs has also progressed.

For instance, ball grid array (BGA) technology has been developed to allow for more densely spaced contacts on an IC device. The use of BGA technology involves placement of solder balls at attachment pads of a PCB. An IC device may be positioned such that the contact pads of the IC device contact the solder balls. The assembly is then heated such that the solder melts, affixing the IC device to the PCB such that electrical contact is established between the IC device and the PCB. This process of heating the solder to affix an IC device to a PCB is commonly referred to as reflow.

However, with the development of BGA technology, a new failure mode has also been discovered. This failure mode corresponds to fracturing of a PCB substrate underneath an attachment pad of the PCB that may in turn lead to the attachment pad becoming separated from the PCB. This process of fracturing and separation of the PCB substrate below the attachment pad is referred to as PCB cratering. Cratering is undesirable because, once cratering occurs, the electrical connection established between the IC device and the PCB may be interrupted such that the IC device may be rendered inoperable.

In response to the discovery of the potential for PCB cratering, tests have been proposed to evaluate PCB designs and materials. Generally, these tests include pin-pull tests, ball-pull tests, and ball-shear tests. Using these tests, PCB designs and materials may be evaluated to determine the susceptibility of PCB designs and materials to experience cratering. These tests may also be used to evaluate the ability of a PCB design or material to withstand cratering.

However, the methodologies and equipment to perform these tests that have been developed to date are unfavorable because the methodology and equipment to perform the tests involve specially designed test equipment to perform the tests. Such specially designed test equipment is expensive. Furthermore, the test equipment is specifically designed to perform PCB catering tests only, thus the equipment is of limited use for tests other than PCB cratering. Moreover, the specially designed test equipment may require specially adapted pins for use with the specially designed test equipment. In this regard, not only does the specially designed test equipment present high initial overhead cost due to the high cost of the specially designed test equipment, but also, because of the specially adapted pins that must be used with the specially designed test equipment, there is also a high continuing overhead cost associated with testing. Accordingly, the ability to test PCB materials and designs for susceptibility to cratering has thus far been an expensive proposition both initially and on an ongoing basis due to the required specially designed test equipment that has thus far been used in cratering tests.

SUMMARY

A first aspect includes a system for testing a printed circuit board (PCB). The system includes a pin having a first end portion and a second end portion. The pin includes a proximal portion that is one of either the first end portion or the second end portion and is operatively engaged by a tensile tester. The system also includes a PCB having at least one attachment pad. A distal portion of the pin is operatively affixed the attachment pad. The distal portion is the other of the one of either the first end portion or the second end portion not engaged by the tensile tester. The pin and the PCB undergo relative movement until failure of the PCB.

A number of feature refinements and additional features are applicable to the first aspect. These feature refinements and additional features may be used individually or in any combination. As such, each of the following features that will be discussed may be, but are not required to be, used with any other feature or combination of features of the first aspect.

In one embodiment, the pin may be a generic pin that may be used with a plurality of different types of tensile testers. Furthermore, the pin may be engaged by a jaw structure of the tensile tester. In one arrangement, the distal portion of the pin and the attachment pad may be operatively affixed by a solder connection. The distal end may include a surface finish to promote solder wetting thereon.

In another embodiment, the system may include an external heat source that is selectively contactable with the pin to heat the pin. The external heat source may be a soldering iron. In one arrangement, the failure of the PCB may include cratering of the PCB below the attachment pad. The PCB may include at least one crack adjacent to the attachment pad. The at least one crack may contain dye, such that upon the failure, dye contained in the at least one crack may be exposed.

A second aspect includes a system for testing a printed circuit board (PCB). The system includes a tensile tester having a jaw structure and a work holder. The system also includes a pin having a first end portion and a second end portion. A proximal portion of the pin is one of either the first end portion or the second end portion and is operatively engaged by the jaw structure. The system also includes a PCB operatively engaged by the work holder. The PCB includes at least one attachment pad. The attachment pad and a distal end of the pin are positioned adjacent to each other. The distal end of the pin is the other of the one of either the first end portion or the second end portion not operatively engaged by the jaw structure. The distal end of the pin is operatively affixed to the PCB, and the jaw structure and the PCB undergo relative movement until failure of the PCB.

A number of feature refinements and additional features are applicable to the second aspect of the present invention. These feature refinements and additional features may be used individually or in any combination. As such, each of the following features that will be discussed may be, but are not required to be, used with any other feature or combination of features of the second aspect.

In one embodiment, the work holder may hold the PCB such that the PCB does not substantially flex when the jaw structure and the PCB move relative to one another. The first end portion of the pin may be substantially the same as the second end portion of the pin. In one arrangement, the distal end of the pin may include a surface finish to promote solder wetting thereon. The distal end may be operatively affixed to the attachment pad with a soldered connection. Furthermore, the failure of the PCB may include cratering of the PCB under the attachment pad.

In another embodiment, the system may also include a heating element selectively contactable with the pin. The heating element may be operable to heat the pin to melt solder to form the soldered connection between the distal end and the attachment pad. A projected area of the distal end of the pin may be larger than an area of the attachment pad. Additionally, the PCB may include at least one crack adjacent to the attachment pad, and the at least one crack may contain dye such that upon the failure of the PCB, dye contained in the at least one crack is exposed.

A third aspect includes a method for testing printed circuit board (PCB) materials and designs. The method involves grasping a pin with a jaw structure of a tensile tester, aligning the pin with an attachment pad of a PCB, and soldering the pin to the attachment pad of the PCB with a heating element separate from the tensile tester to operatively affix the pin and the PCB. The method of the third aspect further involves removing the heating element from contact with the pin and moving the jaw structure and the PCB relative to one another until failure of the PCB.

A number of feature refinements and additional features are applicable to the third aspect of the present invention. These feature refinements and additional features may be used individually or in any combination. As such, each of the following features that will be discussed may be, but are not required to be, used with any other feature or combination of features of the third aspect.

In one embodiment, a proximal end of the pin comprising one of either a first portion or a second portion of the pin may be operatively engaged by the jaw structure. The grasping may include closing the jaw structure on the proximal end of the pin. A distal end of the pin may be soldered to the attachment pad of the PCB. The distal end of the pin may be the other of the one of either the first portion or the second portion not engaged by the jaw structure. The pin may be useable in a plurality of different tensile testers.

Furthermore, in one embodiment, the aligning may include positioning the distal end of the pin adjacent to an attachment pad of the PCB. The heating element may be a soldering iron. In one embodiment, the failure of the PCB may include cratering of the PCB adjacent to the attachment pad.

In another embodiment, the method of the third aspect may include applying dye to the PCB prior to the soldering and removing the dye from a surface of the PCB. Upon the failure, dye confined in cracks existing in the PCB prior to the moving may be exposed.

DETAILED DESCRIPTION

Figure 1:
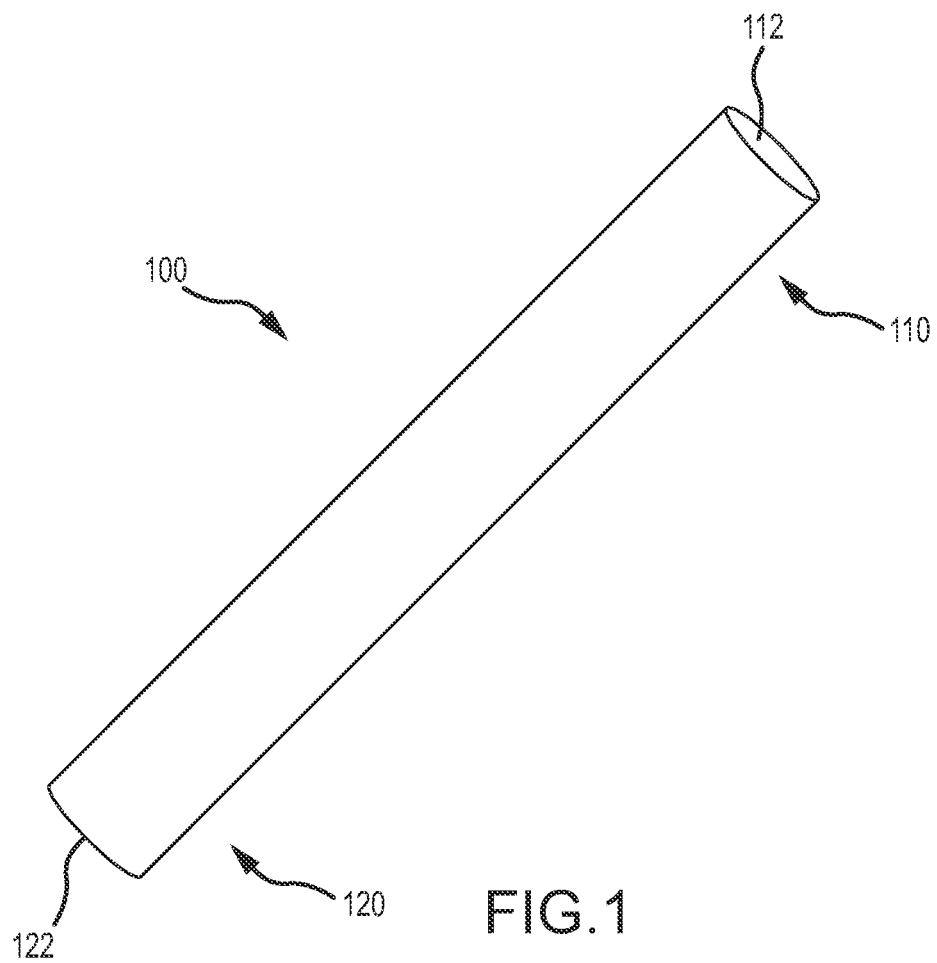
FIG. 1 is a perspective view of a pin that may be used in pin-pull testing.

While the invention is susceptible to various modifications and alternative forms, specific embodiments thereof have been shown by way of example in the drawings and are herein described in detail. It should be understood, however, that it is not intended to limit the invention to the particular form disclosed, but rather, the invention is to cover all modifications, equivalents, and alternatives falling within the scope and spirit of the invention as defined by the claims. Furthermore, the figures referenced herein are for illustrative purposes and are not to scale.

The embodiments presented generally facilitate pin-pull testing for evaluation of the susceptibility of PCB designs and materials to experience cratering of a PCB at an attachment pad of the PCB. The embodiments presented herein are further intended to provide low-cost, high-efficiency methods and apparatus capable of performing pin-pull testing without the need for specifically designed apparatus that employ specially adapted pins for engagement with the specially adapted apparatus to perform pin-pull testing. In this regard, testing may be accomplished using commonly available equipment that has functions other than PCB testing, thus assisting in alleviating the costs associated with existing methods of PCB testing.

One embodiment of a pin that may be used for pin-pull testing is depicted in FIG. 1. The pin 100 generally includes a first end portion 110 and a second end portion 120. The first end portion 110 and second end portion 120 may be substantially the same such that the pin may be substantially the same at both the first end portion 110 and the second end portion 120. The first end portion 110 may terminate in a first end 112. The second end portion 120 may terminate at a second end 122. One skilled in the art will appreciate that due to the substantially similar nature of the first end portion 110 and second end portion 120, either portion may be used such that one end of the pin 100 may be engaged by a common tensile tester. Additionally, the first end portion 110, the second end portion 120, or both may include a surface finish that promotes solder wetting. In turn, solder may be applied to an end of the pin in preparation of conducting a test. While the pin 100 is shown as having blunt ends, the ends of the pin 100 may take other shapes. For example, in one embodiment, the pin 100 may include rounded ends.

Either end of the pin 100 may be engaged by the jaws of a tensile tester to be used in a pin-pull test. Furthermore, as the pin 100 does not include special features or characteristics to provide engagement of the pin 100 with a tensile tester, one skilled in the art will appreciate that a number of different kinds of tensile testers may be used in conjunction with the pin 100 to perform pin-pull tests. Generally speaking, any tensile tester capable of grasping a pin may be used this regard. That is, the pin 100, due to its generic features, may be used in any number of different kinds of tensile testers commonly available in material laboratories. Such a generic pin 100 may lack specifically adapted connection features to facilitate connection with a specific tensile tester or other specifically designed testing machine. In turn, the pin may be less expensive to purchase or manufacture than a pin incorporating such features.

Figure 2A:
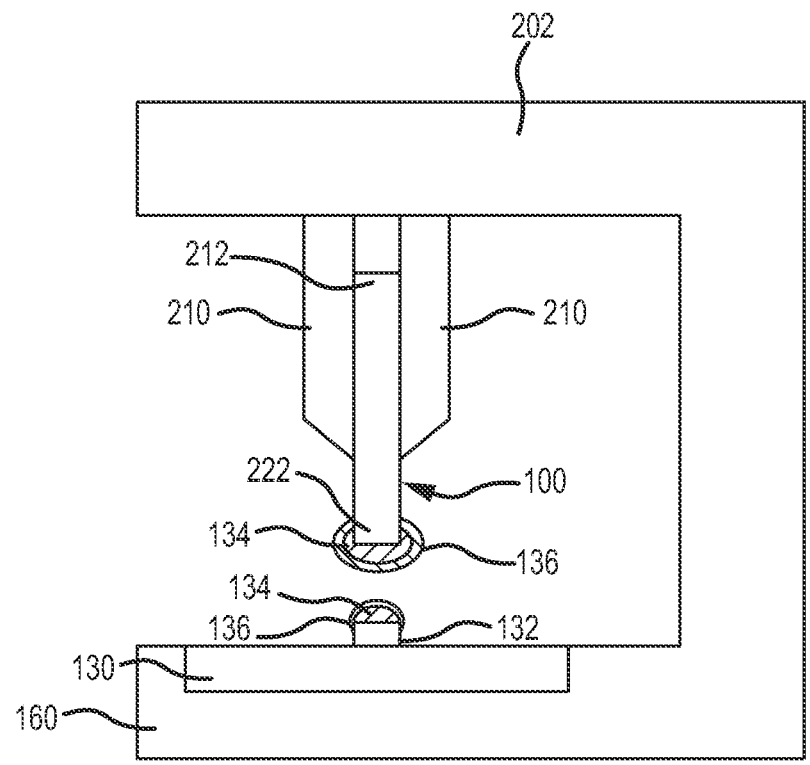
FIGS. 2A-F are front sectional views of a testing apparatus during various instances during the testing of a PCB.

FIGS. 2A-2F depict a testing apparatus during a sequence of steps that may be performed to conduct a pin-pull test. In FIG. 2A, a pin 100 is engaged by jaw members 210 of a tensile tester 202. The tensile tester 202 used may be a standard tensile tester commonly available in materials testing laboratories. The tensile tester 202, having jaw members 210 may be used for a variety of tensile tests aside from pin-pull tests. That is, the jaw members 210 may not include specific attachment features to accommodate the pin 100, but may simply grasp the pin 100 between the jaw members 210. In any regard, a proximal end 212 of the pin 100 may be engaged by the jaw members 210. The proximal end 212, as discussed above, may be either of the first end portion 110 or second end portion 112 of a pin as described with reference to FIG. 1. The pin 100 may include solid solder 134 and flux 136 disposed at a distal end 222 of the pin 100. The distal end 222 may be the other end of a pin 100 as described with respect to FIG. 1. In this respect, the distal end 222 may be the other end of the first and second end portions 110, 112 not engaged by the jaw members 210.

Additionally, a PCB substrate 130 may be provided. The PCB substrate 130 may be affixed to a work holder 160 that in turn maybe operatively engaged with another portion of the tensile tester 202. The work holder 160 may comprise a vice, vacuum table, fixture, or other means for attaching the PCB substrate 130 to the tensile tester 202 or otherwise rigidly holding the PCB substrate 130 during the pin-pull test. For instance, work holder 160 may comprise a plate adapted to be grasped by another set of jaws (not shown) of the tensile tester 202 or some other means of securing the plate. In any regard, the work holder 160 may prevent the PCB substrate 130 from substantially flexing during the pin-pull test.

The PCB substrate 130 may include an attachment pad 132. The attachment pad 132 may be an attachment pad produced in a similar manner to those found on production PCBs. Alternatively, the attachment pad 132 may incorporate experimental PCB materials or designs for evaluation. The PCB substrate 130 may be produced in a batch or sheet process wherein many PCBs are printed onto a single sheet. Individual PCBs may then be separated from the sheet to form PCB coupons (i.e., portions of PCB segmented from the sheet). While a single attachment pad 132 is depicted in the figures, one of ordinary skill in the art will appreciate that a PCB coupon having a number of attachment pads for testing may be provided. The attachment pad 132 may include an amount of solid solder 134 as well as flux 136. The jaw members 210 and work holder 160 may be moved with respect to one another such that the pin 100 is generally aligned with the PCB substrate 130 (e.g., the pin 100 may be adjacent to and in line with the attachment pad 132). In one embodiment, the projected area of the pin 100 is as large as or larger than the projected area of the attachment pad 132.

Figure 2B:
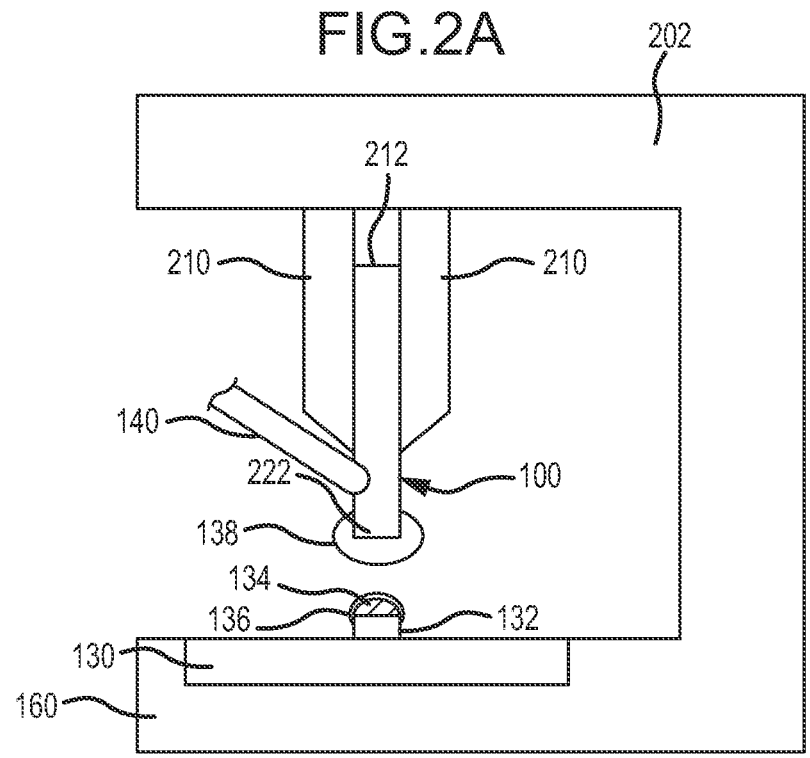

In FIG. 2B, an external heat source 140 may be applied directly to the pin 100. The external heat source 140 may be a separate unit from the tensile tester 202, pin, or PCB substrate. In this regard, the external heat source 140 may be a heat source commonly found in most materials testing laboratories. In one embodiment, the heat source 130 may be a soldering iron. Accordingly, the external heat source may be used in other applications aside from the PCB testing. Thus, the tensile tester 202 used in the PCB testing may not include an integrated heat source that is dedicated to heating of pins retained by the tester. In any regard, the external heat source 140 may contact the pin 100 such that the external heat source 140 heats the pin 100. As such, the distal end 222 previously including solid solder 134 may also be heated such that the solid solder 134 undergoes a phase transformation to liquid solder 138.

Figure 2C:
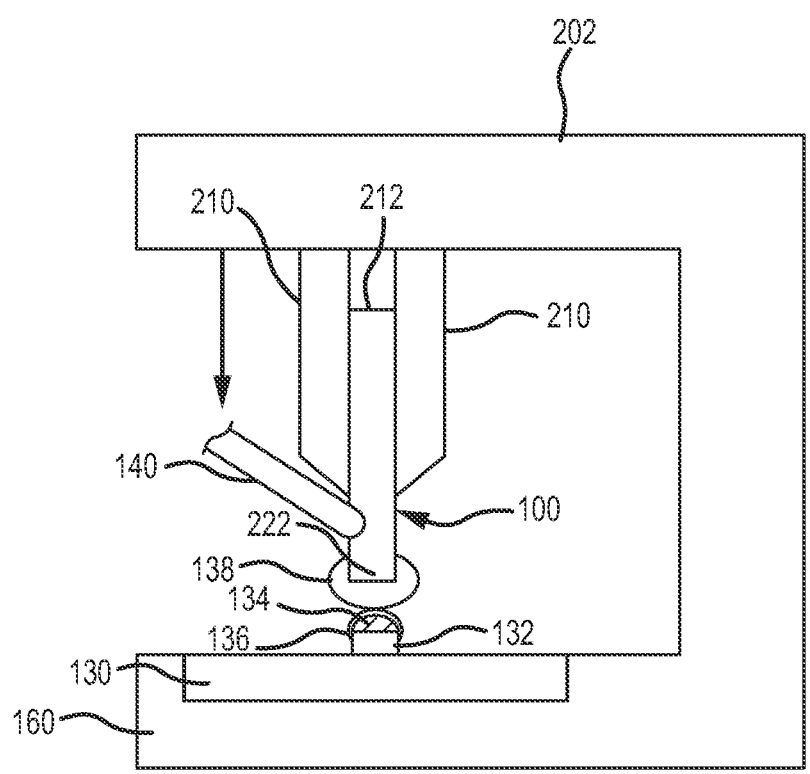
Figure 2D:
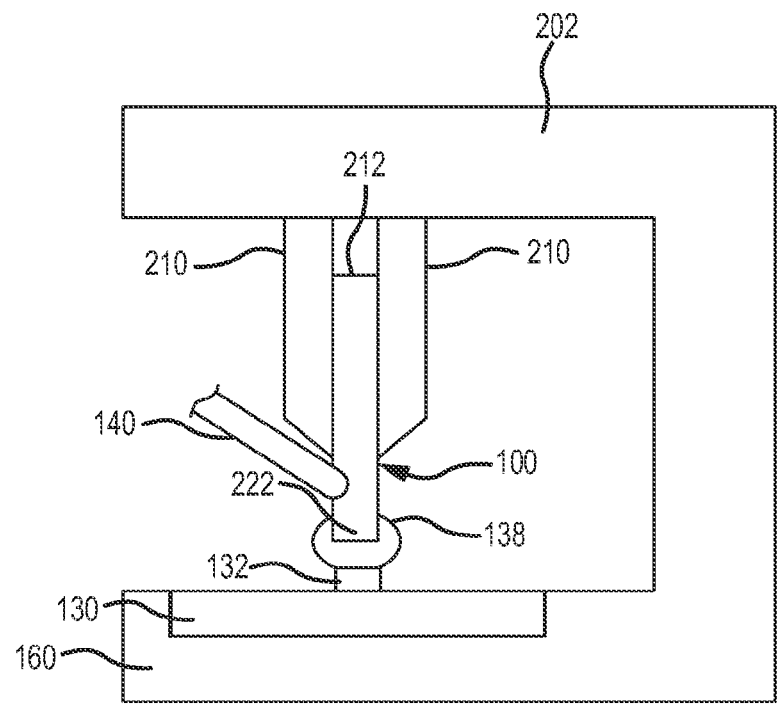

In FIG. 2C, the jaw members 210 have been moved with respect to the work holder 160 in the direction of the arrow such that the pin 100 may be positioned adjacent to the attachment pad 132. The external heat source 140 may still be applied to the pin 100 such that the pin 100 remains heated and maintains liquid solder 138 upon the distal end thereof. The liquid solder 138 may be brought into proximity with the flux 136 and solid solder 134 on the attachment pad 132. In this regard, the solid solder 134 on the attachment pad 132 may also be heated by way of the application of the external heat source to the pin 100 and the solder 134 on the attachment pad 132 may also undergo a phase change such that liquid solder 138 is disposed between the attachment pad 132 and the distal end 222 of the pin 100, as shown in FIG. 2D. The external heat source 140 may continue to be applied to the pin 100 for a certain amount of time to ensure all solder becomes liquid solder 138 between the attachment pad 132 and distal end 222.

Figure 2E:
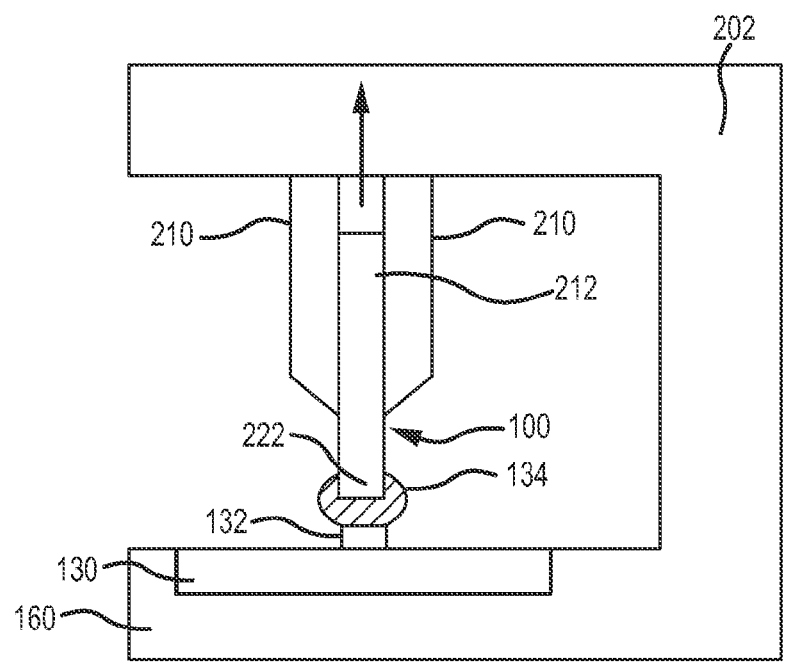

In FIG. 2E, the external heat source 140 may be removed such that the pin 100 may be allowed to cool. Thus, the liquid solder 138 disposed between the attachment pad 132 and distal end 222 may solidify into solid solder 134 such that the attachment pad 132 may be affixed to the distal end 222 of the pin 100 by way of a solid solder attachment 170. The pin 100 may be attached to the PCB substrate 130 by way of the attachment 170 at the attachment pad 132.

After the solder 134 has cooled, the jaw members 210 may be generally moved away from the work holder 160 in a direction represented by the arrow in FIG. 2E. It will be understood by those skilled in the art that jaw members 210 need not be moved away from the work holder 160, but rather any relative movement between the work holder 160 and the jaw members 210 may suffice. That is, the work holder 160 may be moved away from the jaw members 210, the jaw members 210 may be moved away from the work holder 160, or a combination of relative movement may occur.

Figure 2F:
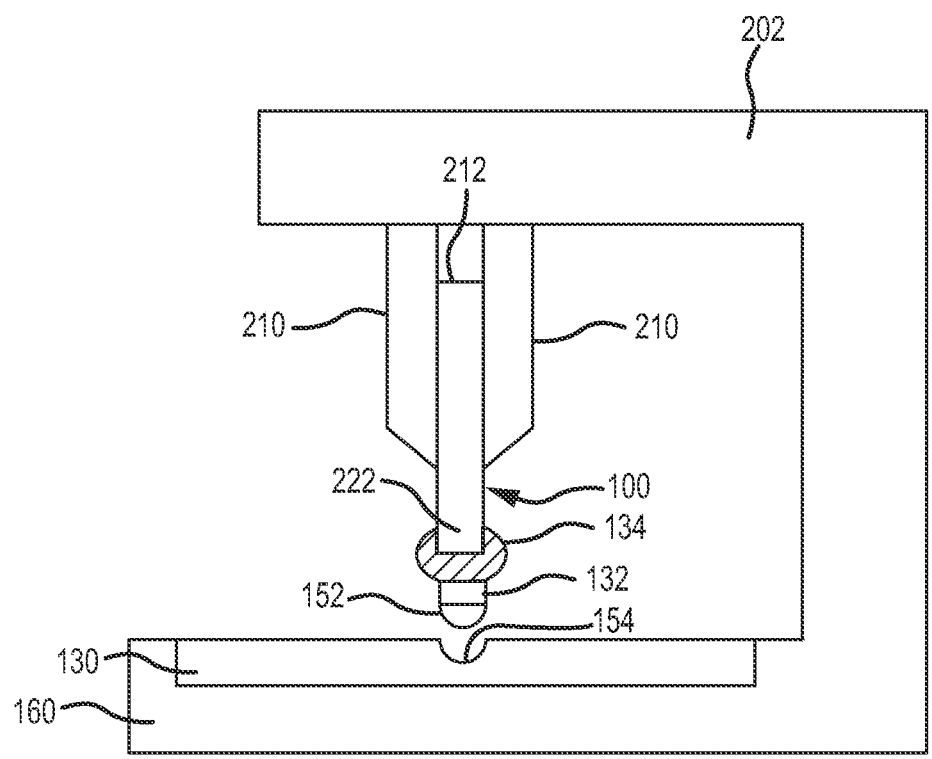

In any regard, as shown in FIG. 2F, the jaw members 210 may be moved with respect to the work holder 160 such that a failure of the PCB substrate 130 occurs. The attachment pad 132 as well as a portion of fractured PCB material 152 may be removed from the PCB substrate 130. This may result in a crater 154 on the PCB substrate 130 at the point of failure.

During the movement of the jaw member 210 from the arrangement depicted in FIG. 2E to the arrangement pictured in FIG. 2F, the force acting on the attachment 170 may be recorded such that a maximum force exerted on the on the attachment 170 prior to failure of the PCB substrate 130 is recorded. For instance, a strain gauge or other apparatus may be included on the tensile tester 202 that is operative to record the force acting on the attachments 170. In turn, data may be gathered that assists in analysis to determine the relative ability of a PCB substrate to withstand cratering.

Figure 3:
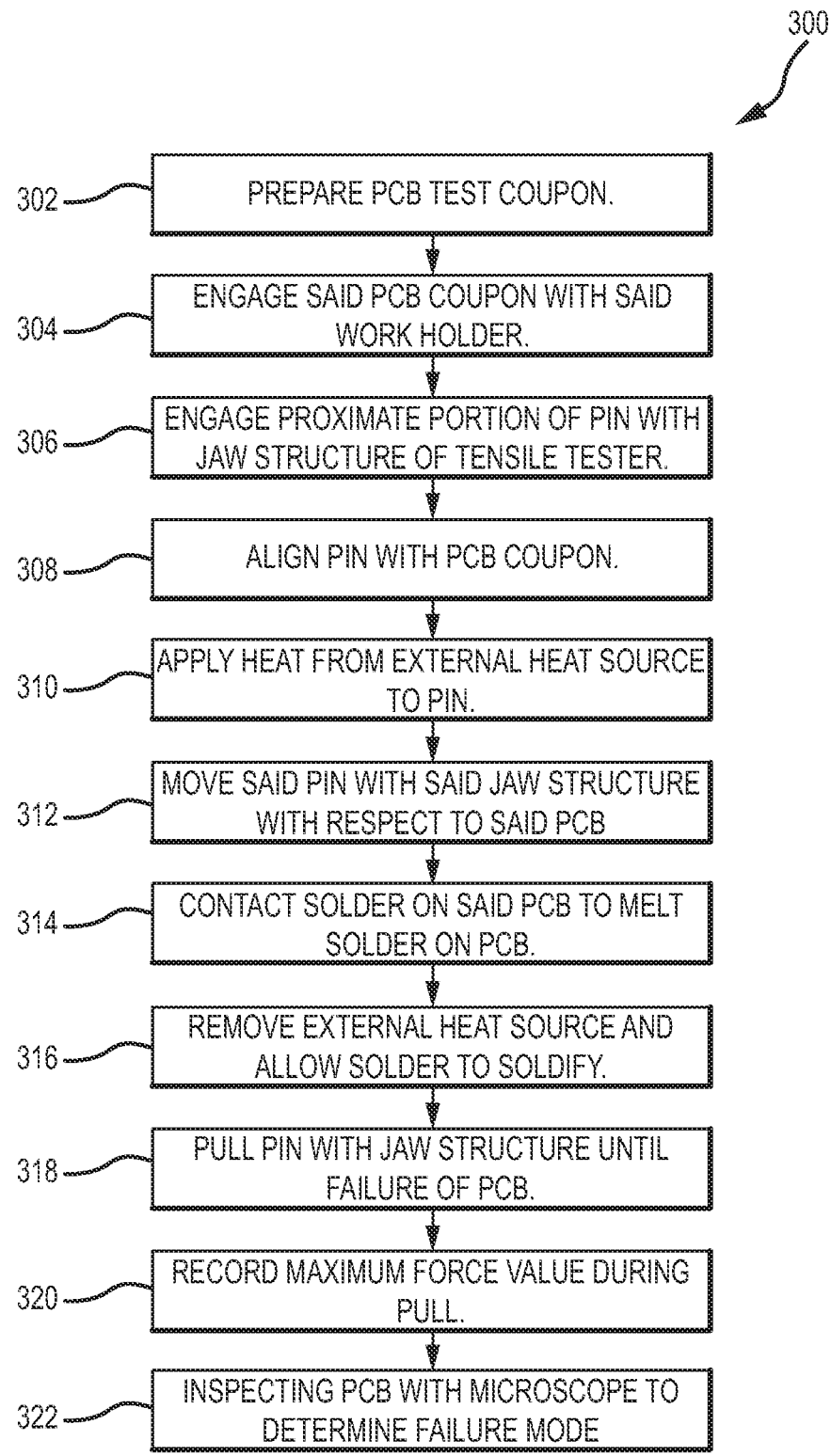
FIG. 3 is a flow chart depicting an exemplary process for testing a PCB.

FIG. 3 depicts a flow chart of an exemplary process 300. The process 300 may include preparing 302 a PCB test coupon that is to be tested. It will be understood that multiple test sites may be prepared on a PCB test coupon. Furthermore, multiple PCB test coupons may be manufactured with varying use of materials and PCB designs such that the different materials and designs may be evaluated for susceptibility of cratering using the process 300.

The process 300 further includes engaging 304 the PCB coupon with a work holder of a tensile tester. Additionally, the process 300 includes engaging 306 a proximal portion of a pin by a tensile tester. Furthermore, the pin may be aligned 308 with the PCB coupon.

The process may include applying 310 heat from an external heat source to the pin. Applying heat 310 may result in solder that is affixed to either the pin 100, the PCB coupon, or both being heated such that liquid solder is produced that enables the pin to be soldered to PCB coupon. As such, the pin may be moved 312 with respect to the PCB such that the pin is moved to be adjacent to the PCB at an attachment point thereof. In this regard, solder on the PCB may be contacted 314 such that the solder is melted. Although heating is discussed prior to moving, one of ordinary skill in the art will understand that movement may occur first (e.g., the pin may be placed adjacent to the attachment pad and subsequently heated or vice versa).

The external heat source may be removed 316 such that the solder melted during the contacting 314 is allowed to solidify. Thus, the removing 316 may result in a solid solder joint between the pin and an attachment pad of the PCB coupon, once the solder disposed between the pin and attachment pad have been allowed to cool.

The process 300 may further include pulling 318 the pin with the jaw structure until failure of the PCB. During the pulling 318 the force applied to the assembly may be recorded 320 such that the maximum force value experienced during the test is recorded. In this regard, results that were recorded 320 during the test may be used for analysis to determine the performance of the PCB coupon prior to cratering of the PCB coupon. As multiple PCB coupons may be prepared and tested, a plurality of designs or PCB materials may be tested using the method 300.

Furthermore, the process 300 may include inspecting 322 the PCB with a microscope once the test has been conducted. In this regard, the failure mode of the PCB may be determined. For example, the severity of the catering (e.g., the number of layers of PCB substrate that failed, etc.) may be determined. Furthermore, in some instances, the solder connection may fracture such that the PCB does not in fact crater. Such a result may be observed during the inspecting 322 to determine the failure mode and the results obtained from such a test may be treated appropriately.

In addition to quantifying the force a PCB may withstand prior to cratering, it may also be advantageous to determine the state of the PCB prior to the destructive testing. For example, in the production of the PCB (e.g., when forming or processing an attachment pad), cracks may develop adjacent to the attachment pad. The formation of cracks in the PCB substrate adjacent to the attachment pad may affect the ability of the PCB substrate to withstand cratering. Thus, it may be desirable to evaluate the presence of cracks adjacent to the attachment pad that exist prior to PCB testing.

In this regard, a PCB coupon may be prepared prior to testing such that pre-existing cracks (e.g., micro cracks not visible with the human eye) existing in PCB substrate prior to testing may be detected after testing has been completed. One example of such a process is depicted in FIGS. 4A-D and 5. The process generally involves applying a dye onto the surface of the PCB. The dye may then seep or flow into preexisting cracks. The surface of the PCB may be cleaned such that the surface of the PCB is substantially free of dye, but dye remains in the preexisting cracks. In this regard, once the PCB has failed, the dyed portions of the crack that existed prior to testing may retain color such that observation of the crater upon testing may reveal the extent of the crack prior to the testing.

Figure 4A:
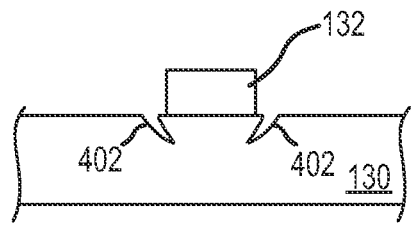
FIGS. 4A-D are front sectional views of a testing apparatus during various instances during a dying process.

FIG. 4A depicts a PCB substrate 130 upon which the dying process may be performed. The PCB substrate 130 may include an attachment pad 132 as was described with reference to FIGS. 2A-2G. During the processing of the PCB substrate 130 to produce the attachment pad 132 or during some other processing of the PCB, cracks such as pre-existing cracks 402 may form surrounding or adjacent to the attachment pad 132.

Figure 4B:
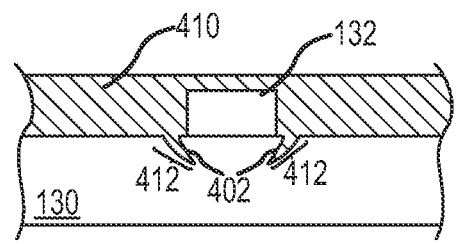
Figure 4C:
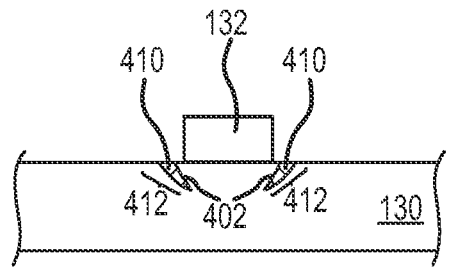

As shown in FIG. 4B, a dye 410 may be applied to the PCB substrate 130. Accordingly, the dye 410 may flow into the pre-existing cracks 402. The PCB substrate 130 may be subjected to a vacuum such that the dye 410 more readily flows into the pre-existing cracks 402. Thus, exposed crack surface 412 of the pre-existing cracks 402 may be dyed. The dye 410 may be allowed to cure. As shown in FIG. 4C, the dye 410 may be removed from the surface of the PCB substrate 130 (e.g., the surface of the PCB may be cleaned). However, dye may be entrained or otherwise captured within the pre-existing cracks 402 after cleaning of the dye 410 from the PCB substrate 130. In this regard, the preexisting cracks 402 may still retain dye 410 after the dye 410 has been removed from the remainder of the PCB substrate 130. Thus, the pre-existing cracks 402 may retain dye 410 that results in the exposed crack surface 412 still being dyed once the remainder of the dye 410 has been removed from the surface of the PCB.

Figure 4D:
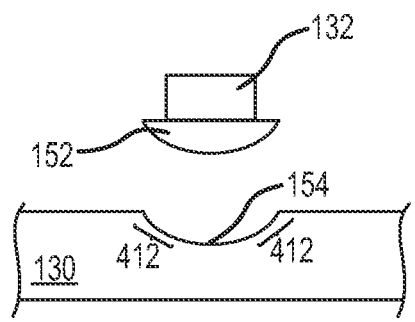

In this regard, after a pin-pull has been conducted, as shown in FIG. 4D, the attachment pad 132 may be separated from the PCB substrate 130 such that a portion of fractured PCB material 152 may remain attached to the attachment pad 132. Accordingly, a crater 154 may be left remaining on the PCB substrate 130. As such, a portion of the crater 154 may comprise the exposed crack surface 412. As the exposed crack surface 412 may have retained dye in the pre-existing cracks 402 after removal the dye 410 from the surface of the PCB substrate 130, the exposed crack surface 412 may retain dye 410. Once exposed by the removal of the fractured PCB material 152, the portion of the crater 154 corresponding to the exposed crack surface 412 may be visible in the crater 154. In this regard, cracks that existed prior the test may be dyed, whereas newly fractured PCB substrate that fractured during the pin-pull test may be substantially free of dye.

Figure 5:
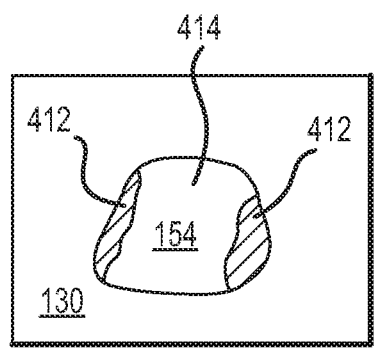
FIG. 5 is a top view of a PCB crater.

FIG. 5 shows a top view of the failed PCB substrate 130 after the test has been performed. The crater 154 may include regions corresponding to the exposed crack surface 412. Thus, the regions where pre-existing cracks 402 existed prior to the test are exposed such that the dyed portions of the exposed crack surface 412 are visible. However, PCB substrate that fractured during the test 414 may be substantially free of dye. Thus, the presence of pre-existing cracks 402 may be evaluated after the test is been completed. That is, the portion of the crater 154 which existed (in the form of a pre-existing crack 402) may have been exposed to the dye in the dying process, whereas material that fractured during the test 414 (i.e., after the dying process has been completed) may not have been exposed to the dye. In this regard, observation of the crater 154 after the testing and dying may allow for evaluation of the extent of cracks that existed prior to the testing. As such, this information regarding the extent of pre-existing cracks 402 prior to the test may facilitate evaluation of the PCB materials and design. For example, extensive pre-existing cracks 402 may indicate the PCB was flawed due to a manufacturing defect or similar quality issue. Furthermore, by studying the extent to which a PCB is cracked prior to engaging in pin-pull testing, the manufacturing process, material selection, and PCB design may be improved to reduce the presence of pre-existing cracks 402.

In sum, one skilled in the art will recognize that by using a tensile tester with standard jaw construction and generic pins, the high overhead costs associated with specialty testing devices employing specially adapted pins may be overcome. In this regard, tensile testers commonly available in material testing laboratories may be employed in order to evaluate the susceptibility of PCB materials and designs to succumb to cratering. Not only may the PCB failure tests be performed on cheaper equipment found in existing laboratories, but also the pins employed may not be specifically adapted to a particular machine, and thus cheaper to produce or purchase. In this regard, the overall cost of PCB failure testing for susceptibility of cratering may be lowered while maintaining the ability to perform the tests smoothly with consistent pull force.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences).

Accordingly, it should be understood that only the preferred embodiment and variants thereof have been shown and described and that all changes and modifications that come within the spirit of the invention are desired to be protected.

What is claimed is:

1. A system for testing a printed circuit board (PCB), comprising:
    a pin comprising a first end portion and a second end portion, wherein a proximal portion comprising one of either said first end portion and said second end portion is operatively engaged by a tensile tester;
    a PCB having at least one attachment pad;
    wherein a distal portion of said pin comprising the other of said one of either said first end portion and said second end portion not engaged by said tensile tester is operatively affixed to said attachment pad, and wherein said pin and said PCB undergo relative movement until failure of said PCB; and
    wherein the PCB comprises at least one crack adjacent to said attachment pad, and said at least one crack contains dye, wherein, upon said failure, dye contained in said at least one crack is exposed.

2. The system of claim 1, wherein said pin is a generic pin useable with a plurality of different types of tensile testers.

3. The system of claim 2, wherein said pin is engaged by a jaw structure of said tensile tester.

4. The system of claim 3, wherein said distal portion of said pin and said attachment pad are operatively affixed by a solder connection.

5. The system of claim 1, wherein said distal end comprises a surface finish to promote solder wetting thereon.

6. The system of claim 1, further comprising:
    an external heat source that is selectively contactable with said pin to heat said pin.

7. The system of claim 6, wherein said external heat source comprises a soldering iron.

8. The system of claim 1, wherein said failure comprises cratering of said PCB below said attachment pad.

9. A system for testing a printed circuit board (PCB), comprising:
    a tensile tester having a jaw structure and a work holder;
    a pin having a first end portion and a second end portion, wherein a proximal portion comprising one of either said first end portion and said second end portion is operatively engaged by said jaw structure, and wherein said first end portion of said pin is substantially the same as said second end portion of said pin;
    a PCB operatively engaged by said work holder, said PCB comprising at least one attachment pad, wherein said attachment pad and a distal end of said pin comprising the other of said one of either said first end portion and said second end portion not operatively engaged by said jaw structure are positioned adjacent to each other;
    wherein said distal end of said pin is operatively affixed to said PCB, and said jaw structure and said PCB undergo relative movement until failure of said PCB; and
    wherein said PCB comprises at least one crack adjacent to said attachment pad, and said at least one crack contains dye, wherein, upon said failure, dye contained in said at least one crack is exposed.

10. The system of claim 9, wherein said work holder holds said PCB such that said PCB does not substantially flex when said jaw structure and said PCB move relative to one another.

11. The system of claim 9, wherein said distal end of said pin comprises a surface finish to promote solder wetting thereon.

12. The system of claim 11, wherein said distal end is operatively affixed to said attachment pad with a soldered connection.

13. The system of claim 12, wherein said failure of said PCB comprises cratering of said PCB under said attachment pad.

14. The system of claim 9, further comprising:
    a heating element selectively contactable with said pin.

15. The system of claim 14, wherein said heating element is operable to heat said pin to melt solder to form said soldered connection between said distal end and said attachment pad.

16. The system of claim 9, wherein a projected area of said distal end of said pin is larger than an area of said attachment pad.

17. A method for testing printed circuit board (PCB) materials and designs, comprising:
    applying dye to said PCB prior to said soldering;
    removing said dye from a surface of said PCB;
    grasping a pin with a jaw structure of a tensile tester;
    aligning said pin with an attachment pad of a PCB;
    soldering said pin to said attachment pad of said PCB with a heating element separate from said tensile tester to operatively affix said pin and said PCB;
    removing said heating element from contact with said pin; and
    moving said jaw structure and said PCB relative to one another until failure of said PCB;
    wherein upon said failure, dye confined in cracks existing in said PCB prior to said moving is exposed.

18. The method of claim 17, wherein a proximal end of said pin comprising one of either a first portion and a second portion of said pin is operatively engaged by said jaw structure, and wherein said grasping comprises closing said jaw structure on said proximal of said pin, and a distal end of said pin comprising the other of said one of either said first portion and said second portion not engaged by said jaw structure is soldered to said attachment pad of said PCB.

19. The method of claim 18, wherein said pin is useable in a plurality of different tensile testers.

20. The method of claim 18, wherein said aligning comprises positioning said distal end of said pin adjacent to an attachment pad of said PCB.

21. The method of claim 20, wherein said heating element comprises a soldering iron.

22. The method of claim 21, wherein said failure comprises cratering of said PCB adjacent to said attachment pad.

* * * * *